(12) United States Patent
Yu et al.

(10) Patent No.: US 11,331,079 B2
(45) Date of Patent: May 17, 2022

(54) METHOD AND DEVICE FOR PROCESSING ULTRASOUND SIGNAL DATA

(71) Applicant: KONINKLIJKE PHILIPS N.V., Eindhoven (NL)

(72) Inventors: Tong Nicolas Yu, Eindhoven (NL); Sheng-Wen Huang, Ossining, NY (US); Francois Guy Gerard Marie Vignon, Andover, MA (US); Oudom Somphone, Paris (FR); Shiying Wang, Melrose, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 123 days.

(21) Appl. No.: 16/628,887

(22) PCT Filed: Jul. 9, 2018

(86) PCT No.: PCT/EP2018/068478
§ 371 (c)(1),
(2) Date: Jan. 6, 2020

(87) PCT Pub. No.: WO2019/008187
PCT Pub. Date: Jan. 10, 2019

(65) Prior Publication Data
US 2020/0229797 A1    Jul. 23, 2020

(30) Foreign Application Priority Data

Jul. 7, 2017 (EP) .................................... 17305885

(51) Int. Cl.
*A61B 8/08* (2006.01)
*A61B 8/14* (2006.01)
(Continued)

(52) U.S. Cl.
CPC ............ *A61B 8/5246* (2013.01); *A61B 8/145* (2013.01); *A61B 8/4488* (2013.01);
(Continued)

(58) Field of Classification Search
CPC .... A61B 8/5207; A61B 8/5276; G06T 7/0012
See application file for complete search history.

(56) References Cited

U.S. PATENT DOCUMENTS 6,524,252 B1   2/2003  Yu et al.
8,107,694 B2   1/2012  Hamilton et al.
(Continued)

OTHER PUBLICATIONS

Rognin, et al., "A new approach for automatic motion compensation for improved estimation of perfusion quantification parameters in ultrasound imaging", CFA 2006, Jan. 1, 2006, pp. 61-65.
(Continued)

*Primary Examiner* — Ashley K Buran
*Assistant Examiner* — Sean V Blinder

(57) ABSTRACT

The invention provides an ultrasound data processing method for pre-processing signal data in advance of generating ultrasound images. The method seeks to reduce noise through application of coherent persistence to a series of raw ultrasound signal representations representative of the same path or section through a body but at different successive times. A motion compensation procedure including amplitude peak registration and phase alignment is applied to raw echo signal data in advance of application of persistence in order to cohere the signals and thereby limit the introduction of motion induced artifacts.

18 Claims, 8 Drawing Sheets

(51) Int. Cl.
 *A61B 8/00* (2006.01)
 *G06T 7/00* (2017.01)
(52) U.S. Cl.
 CPC .......... *A61B 8/5207* (2013.01); *A61B 8/5276* (2013.01); *G06T 7/0012* (2013.01); *G06T 2207/10132* (2013.01)

(56) References Cited

U.S. PATENT DOCUMENTS

| | | | |
|---|---|---|---|
| 8,290,061 | B2 | 10/2012 | Sang et al. |
| 9,754,185 | B2* | 9/2017 | Ikeda ............... H04N 5/232935 |
| 10,321,896 | B2* | 6/2019 | Herzog ............. A61B 5/14546 |
| 2013/0245445 | A1 | 9/2013 | Kakee et al. |
| 2015/0023561 | A1 | 1/2015 | Hamilton |
| 2015/0099975 | A1* | 4/2015 | Lam .................... G01S 7/52077 600/443 |
| 2017/0042511 | A1* | 2/2017 | Labyed ................ A61B 8/5207 |
| 2017/0124426 | A1* | 5/2017 | Li ........................ A61B 8/5223 |

OTHER PUBLICATIONS

Gammelmark, et al., "Duplex Synthetic Aperture Imaging with Tissue Motion Compensation", 2003 IEEE Ultrasonics Symposium Proceedings, Honolulu, Hawaii, Oct. 5-8, 2003, vol. 2, Oct. 5, 2003, pp. 1569-1573.
Simon, et al., "Motion compensation algorithm for non-invasive two-dimensional temperature estimation using diagnostic pulse-echo ultrasound", Visual Communications and Image Processing, Jan. 1, 1998, vol. 3249, pp. 182-192.
International Search Report and Written Opinion for International Application No. PCT/EP2018/068478, filed Jul. 9, 2018, 15 pages.
Wang, et al., "Adaptive Persistence Utilizing Motion Compensation for Ultrasound Images", The 18th International Conference on Pattern Recognition (ICPR'06), IEEE Computer Society, 4 pages.
Somphone, et al., "Fast Myocardial Motion and Strain Estimation in 3D Cardiac Ultrasound with Sparse Demons", 2013 IEEE 10th International Symposium on Biomedical Imaging, Jul. 15, 2013, 4 pages.

\* cited by examiner

METHOD AND DEVICE FOR PROCESSING ULTRASOUND SIGNAL DATA

RELATED APPLICATIONS

This application is the U.S. National Phase application under 35 U.S.C. § 371 of International Application No. PCT/EP2018/068478, filed on Jul. 9, 2018, which claims the benefit of European Application No. 17305885.0, filed Jul. 7, 2017. These applications are hereby incorporated by reference herein.

FIELD OF THE INVENTION

This invention relates to a method for processing ultrasound signal data for generating ultrasound images, and device for the same.

BACKGROUND OF THE INVENTION

Persistence is a technique used in ultrasound data processing for reducing signal noise and improving the quality of resulting ultrasound images. Persistence, in its simplest form, is a process of temporal averaging over multiple successive frames to weaken noise artifacts. It is known from many conventional ultrasound scanners to apply persistence to B-mode or color-flow images. The input provided to the persistence process in such examples is post envelope-detection (amplitude extracted) or post color-processing signal data. Persistence when applied to such data results in an incoherent averaging of the signal frames.

When applied in the case of B-mode imaging, such incoherent persistence can suppress noise in ultrasound data, but its effectiveness in improving the signal-to-noise ratio (SNR) is relatively poor.

An improved signal processing procedure is therefore required which can achieve greater improvement in signal to noise ratio.

SUMMARY OF THE INVENTION

The invention is defined by the claims.
It is possible, instead of the above approach, to apply persistence to raw ultrasound echo data (e.g. RF or IQ data). This is an example of coherent averaging, and has been found to achieve significantly improved results in terms of SNR increase. However, this approach has typically not been considered, since it is highly vulnerable to motion-induced artifacts in the resulting averages due to destructive interferences occurring when the raw signals are summed. This means that either the transducer probe must be held extremely still when capturing the data so as not to introduce motion shifts between frames (which can be impractical) or a very small persistence kernel has to be used (that is, the number of frames included in the average has to be kept very small).

Embodiments of the invention seek to provide a coherent persistence based approach to signal processing but in which motion artifacts are reduced.

According to examples in accordance with an aspect of the invention, there is provided a method of processing ultrasound signal data for use in generating ultrasound images, comprising: receiving a series of data representations of raw echo-signals, each representative of the same trajectory, section or volume through a body but at different successive times; applying a motion compensation procedure to the data representations, the procedure comprising registering amplitude peaks of the raw signals represented by the data representations to one another, and aligning phases of the raw signals to one another; and applying an averaging technique to one or more subsets of the motion-compensated signal representations to thereby derive one or more averaged raw echo-signal representations.

Embodiments of the invention are based on the concept of applying persistence to raw (non-envelope extracted) ultrasound signal data, but wherein that data has been pre-processed with a motion-compensation procedure. In particular, the motion compensation procedure includes registering the amplitudes of the temporally successive ultrasound signals to one another and aligning phases of the ultrasound signals to one another. It has been found that simply performing standard 'frame' registration (which concerns aligning only the signal amplitudes) leaves the resulting set of signals incoherent, which means that subsequent averaging of the signals still results in destructive interferences (which manifest in the final rendered ultrasound images as black stripes and cracks). Hence, embodiments of the present invention propose to align also the phases, leaving the resulting signal set coherent, such that persistence may be applied without introducing motion artifacts. The amplitude peak registration and phase alignment may be performed together in a single step in accordance with certain examples, for instance using cross-correlation of (phase-rich) ultrasound data. However, in preferred examples, they may be performed as two distinct steps.

In particular, in accordance with one or more embodiments, the motion compensation procedure comprises a two-step process, comprising first registering amplitude peaks of the raw signals represented by the data representations to one another, and subsequently applying a phase correction procedure to align the phases of the raw signals to one another.

Here, motion between frames is essentially adjusted in two stages: one correcting amplitude peaks, the second correcting phases. This approach is far more efficient than for instance using cross-correlation, the latter of which is computationally much more costly, and also time consuming. Therefore, in addition to being computationally more efficient, performance of motion compensation as a two-stage process (non-phase and then phase) is also faster, making it far more practical and efficient in, for instance, real-time data processing applications (i.e. where data processing is performed in real time as ultrasound data is collected).

The following comments apply to all embodiments of the invention, including both the single step, and two-step motion compensation options described above. Motion compensation in the present context refers to compensating for relative motion between the body through which the path or section passes or which otherwise is captured or represented by the signal data, and the ultrasound transducer(s). For instance, where the signals are projected through part of a human or animal body, motion compensation may be to compensate for movement of one or more anatomical features or structures lying within the body being imaged.

Embodiments include registering 'amplitude peaks' to one another. By this is meant aligning the signal peaks of the raw signals represented by the data representations (i.e. the peaks corresponding to the amplitude of each signal oscillation). These peaks in the raw data will be referred to as amplitude peaks.

By 'raw echo signals' is simply meant echo signals which have not been processed to extract an envelope signal. The term may include non-envelope-extracted data in a number of forms such as RF data or IQ data. The raw echo signals may be fully sampled or may be down-sampled.

For the purposes of the present disclosure, the raw echo signals may frequently be referred to, for brevity, as RF signals or RF data. However, these terms are not to be construed as limiting for any of the described examples or applications of the invention; any usage of RF data or RF signals should be taken to be entirely replaceable by usage instead for instance of IQ data or baseband IQ data or any data form which is representative of raw, non-envelope-extracted echo signals. The functioning of the invention is not dependent upon the particular form of raw signal data used.

Each of the data representations may comprise data corresponding to a single raw echo signal representative of a single path through a body, or may comprise data corresponding to a plurality of echo signals transmitted through a plurality of paths. In the latter case, the paths may be adjacent paths through said body, such that each data representation provides a representation of a section (that is, a cross-section or plane) through the body, or of a volume within a body.

The data representations may be any suitable data representation including by way of non-limiting example a data array. In this case, where the data representation contains data relating to just a single raw signal, this may be a 1D data array, the entries (i.e. data elements) of the single row providing signal strength values at each sampled time interval. Each of these data elements or entries may be referred to simply as a 'sample' of the relevant signal. Where the data representation contains data related to a plurality of signals, the array may comprise a corresponding plurality of rows.

The series of data representations effectively represent a series of (RF) signal temporal 'frames' in the sense that they each correspond to substantially the same path or section through a body being imaged but at successive times (or time periods/intervals). In the present disclosure, the term 'RF frame' may frequently be used for brevity to refer to one of the data representations of the series. The terms may therefore be understood synonymously. Each RF frame corresponds to the same path or section (or volume) through a body to be imaged, but at a different time. Each may contain data samples relating to a single RF signal (for a single path), or multiple signals for multiple paths (preferably thereby defining a section or plane or volume).

Although the data representations are referred to as corresponding to the same path or section but at different times, this may in reality mean different time periods, since the collection of data samples for a single signal is not instantaneous, but extended in time. The different frames (different data representations) hence would each correspond to successive time periods.

In accordance with at least one set of embodiments, a plurality of averaged raw echo-signal representations are generated by said averaging method of the data processing method, and wherein the method further comprises:
processing said plurality of averaged representations to generate a corresponding plurality of averaged envelope signal representations or ultrasound images, and
applying a further averaging technique to said plurality of averaged envelope signal representations or ultrasound images.

In accordance with this example, a hybrid approach is applied, wherein both coherent and incoherent averaging are performed. Motion compensation and persistence are first applied to the raw echo-signal representations in a way which results in a plurality of averaged raw signal representations. These averaged representations are then processed to extract envelope signal data (i.e. to extract data corresponding to an envelope signal, representative of the variation in amplitude of each averaged raw signal). The envelope signal representations are then themselves averaged (incoherent averaging). The result is a hybrid coherent-incoherent persistence procedure which can achieve better signal-to-noise increase than the basic coherent persistence method.

This hybrid method requires the initial (coherent) averaging technique to produce a plurality of coherently averaged raw signal representations, so that these can then be subsequently incoherently averaged. This can be achieved in examples by dividing the initial series of raw echo-signal representations into a plurality of subsets of representations, each independently averaged using the averaging technique. Thus a plurality of (coherently) averaged representations is produced.

In accordance with one or more embodiments, the motion compensation procedure may comprise designating one of the data representations a reference representation, and registering the amplitude peaks of each of the signals of the remaining data representations to the peaks of the signal(s) of the reference representation, and wherein
the representations are received non-simultaneously and the reference representation is designated as the representation most recently received, or the reference representation is designated as a representation mid-way between the most recently received representation and the least recently received representation.

When registering RF signal representations to one another, there is a choice as to how this is to be done. Preferably all signal representations are individually registered to a single representation, that is amplitude peaks of each signal representation of the series is adjusted or aligned to one particular representation selected from within the series. This may be termed the 'reference representation'.

There is a choice as to which is chosen as the reference representation. In a case where the signal data representations are received at different times (for instance when performing real-time data processing), in accordance with one or more examples, one may choose the most recently received representation as the reference representation. This is advantageous because it minimizes the apparent 'time-lag' in subsequent ultrasound images that are generated from the processed data: where signals are aligned to the most recently received signal before averaging, any resulting image represents the appearance of the body at this most recent time (rather than at a time a number of 'frames' in the past).

However, motion compensation is typically less accurate when performed between frames which are greatly temporally separated. In the case where the most recent frame is the reference, the maximum leap distance is equal to the entire size of the averaging kernel.

In accordance with an alternative set of examples therefore, the reference representation may instead be designated as a representation mid-way between the most recent representation in the series and the least recent representation in the series.

By mid-way is meant temporally midway. By mid-way is meant approximately or roughly mid-way. This may be for instance within a central 60% section of the series, or a central 50% section (i.e. a section between points 20% along the way from the ends of the series or points 25% of the way from the ends of the series).

In these examples, at the cost of a few seconds of latency, temporal displacement between motion compensated frames is reduced, and hence motion compensation accuracy increased.

Choosing the reference representation to be at or near the middle of the series means less movement needs to be compensated and so compensating for the motion by adjusting the raw signals may require less distortion of the signals.

In accordance with a further variation on the above, wherein the reference representation is designated as a representation mid-way between the most recently received representation and the least recently received representation, subsequent to deriving the one or more averaged raw echo-signal representations, a motion compensation procedure may be applied to said averaged raw echo signal representations comprising at least registering amplitude peaks of the one or more averaged representations to those of said most recently received data representation.

By adjusting the resulting coherently averaged frame(s) to the most recent frame, the incurred latency should be fully eliminated, while maintaining the benefits of more robust motion compensation.

In accordance with at least one set of embodiments, the motion compensation procedure may comprise: processing the received series of data representations to derive a corresponding series of envelope signal representations, representative of amplitude variations of the echo signals; determining deviations between the envelope signal representations; performing adjustments to the raw echo signal data representations based on said derived deviations, so as to register the amplitude peaks of the different raw echo-signals to one another; and applying the phase correction procedure to the amplitude registered echo-signal representations so as to register the phases of the signal representations to one another. In accordance with this set of embodiments, registering the amplitude peaks of the raw signals is performed based on motion tracking carried out on the corresponding envelope-extracted data. A copy of the raw data may be taken so as to leave one copy intact while a second is envelope-extracted for the purposes of determining the signal deviations.

By 'deviations' between the envelope signal representations may be meant displacements or misalignments between the representations, e.g. displacements or misalignments in the time-domain of the two envelope signal traces. This for example may be misalignments or displacements of peaks or troughs in the envelope signal traces or of any other features or parts of the signals.

Determining the deviations between the envelope signal representations may in accordance with at least one set of examples comprise: determining deviations between temporally consecutive pairs at least a subset of the series of envelope representations, said subset including one representation designated as a reference representation; adding to each of said consecutive deviations a sum of all preceding or succeeding determined deviations up to the reference representation, such as to derive for each envelope representation a cumulative deviations with respect to the reference signal representation, and adjusting the series of raw echo signal representations, based on the determined cumulative deviations for the envelope signals, to thereby achieve registration of amplitude peaks of the raw echo signals.

In these examples, deviations between the signal(s) of each representation and that/those of a reference representation are calculated. This is done on the basis of first calculating deviations between each consecutive pair of neighboring signal representations and then successively summing these (i.e. determining a cumulative sum). The reason for this is that the resulting algorithm is particularly optimized for real-time signal analysis, since addition of each new signal representation to the series requires only determining of one additional deviation for the new added representation and then simply re-summing to determine new cumulative deviations.

As noted above, in accordance with one set of examples, the method may comprise periodically receiving additional raw echo signal representations to be appended to the series of representations, and wherein at least the above outlined example steps for determining the deviations between envelope-signals are re-executed upon the appending of each newly acquired representation. This enables real-time data acquisition and processing. In accordance with one or more further sets of embodiments, the motion compensation procedure may comprise: determining deviations between signal peaks of the raw echo signal representations; performing adjustments to the raw echo signal data representations based on said derived deviations, so as to achieve registration of the amplitude peaks of the different raw echo-signals to one another, and alignment of the phases of the signal representations to one another.

In accordance with these embodiments, deviations between the raw echo signal representations are determined directly. This may be done for example using algorithms of cross-correlation, Doppler processing, speckle tracking or sum of absolute differences. Any other suitable algorithm may also be used.

In accordance with one or more embodiments, the phase correction procedure may comprise: determining a phase shift of the raw echo signals of at least a subset of said series of data representations with respect to a reference representation; and adjusting the phases of each of said echo signals in accordance with the determined phase shifts. Optionally, the phase shifts for each given data representation $f_i$ may be determined based on the expression $$\alpha = \angle(K \otimes (f_0; f_i^*))$$

where a is is a set of phase shifts, K is a convolution kernel, and $f_0$ is the reference data representation.

The data representation $f_i$ in the above expression may be the amplitude-registered data representation. Note that $f_i^*$ represents the complex conjugate.

In accordance with any embodiment of the invention, the data representations may each be representative of fully sampled echo-signal data received from one or more transducers (rather than down-sampled data).

This may improve phase coherence between the RF signals of different data representations, since phase information which is otherwise lost during the down-sampling is instead retained.

In accordance with any embodiment of the invention, the method may further comprise: determining, following said motion compensation procedure, a measure of similarity between the raw echo signal representations; and determining, based on said measure of similarity, a total number of signal representations to be included in each of said one or more subsets to which the averaging technique is applied.

The total number of signal representations included in each of said one or more subsets to which the averaging technique is applied may preferably be positively related to said determined measure of similarity.

In accordance with these examples, a 'confidence measure' (a measure of similarity) may be determined representing a degree to which the signal representations (or 'frames') are properly registered to one another. Based on this confidence measure, the size/length of the averaging kernel (i.e. the number of signal representations to be included in the average) is determined. A low confidence measure (a low measure of similarity) indicates relatively low degree of successful registration and so may lead to a relatively small number of signal representations in the average (so as to minimize the number of motion artifacts generated in the averaged signal representation). Where the signal representations are well registered, the confidence measure may be high and a large number of signal representations may be included in the average, since in this case, motion artifacts are less likely, so a large average is possible. The larger the averaging kernel, the greater the increase in signal to noise ratio obtained, so high quality signal registration is desirable so that this can be achieved.

In accordance with one set of embodiments, compatible with features of any other embodiment described, the averaging technique comprises determining a weighted average of the signals of said motion compensated signal representations, and wherein the method further comprises: determining, following application of said motion compensation procedure, a measure of similarity between each signal representation and the reference signal representation; and determining a weighting factor for each signal representation based on the determined measure of similarity for said representation, the weighting factors for use in determining said weighted average of the series of representations.

Effectively, a confidence measure is determined for each signal representation indicating how well registered the signal representation is with the reference representation, and based on this, a weighting factor is determined for the representation for use in determining the average signal representation. If the signal representation is only poorly correlated with the reference frame, the weighting factor may be low so as to minimize the degree to which the representation may lead to introduction of motion artifacts.

Optionally, said weighting factors may be binary weighting factors, wherein each representation is only included as part of the averaged signal representation in the case that its determined measure of similarity with respect to the reference is above a certain threshold.

In accordance with any embodiment of the present invention, the method may further comprise processing the averaged data representations to form one or more ultrasound images.

Examples in accordance with a further aspect of the invention provide a processing unit adapted to carry out the ultrasound data processing method according to any embodiment or example described in this disclosure or defined in the claims of the application.

Examples in accordance with a further aspect of the invention provide an ultrasound diagnostic imaging system, comprising: an ultrasound transducer array; and an ultrasound processing unit as described above, operatively coupled with the transducer array and adapted to receive data representations of echo signals captured by the transducer array.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
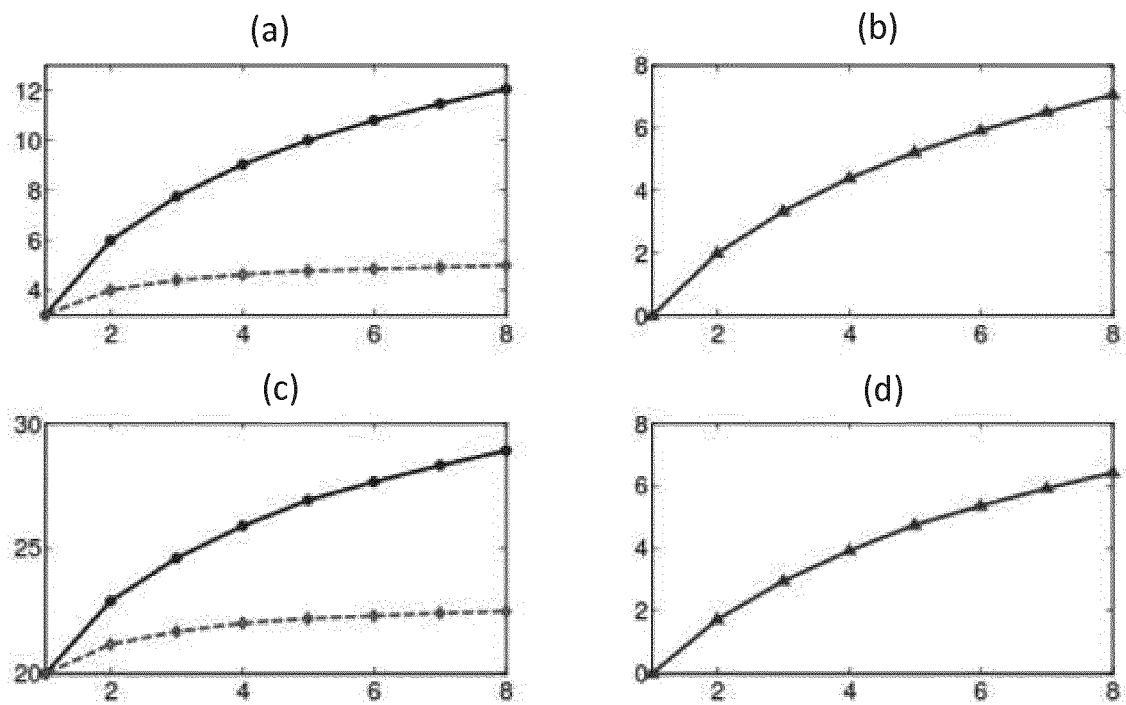
FIG. 1 shows relative signal to noise ratio increase for coherent and incoherent persistence.

The invention provides an ultrasound data processing method for pre-processing signal data in advance of generating ultrasound images. The method seeks to reduce noise through application of coherent persistence to a series of raw ultrasound signal representations representative of the same path or section through a body but at different successive times. A motion compensation procedure including amplitude peak registration and phase alignment is applied to raw echo signal data in advance of application of persistence in order to cohere the signals and thereby limit the introduction of motion induced artifacts.

Embodiments of the invention may be implemented for instance within a signal processing unit of an ultrasound imaging system. Such a signal processing unit may preferably be configured to receive ultrasound echo signals directly and in real time from ultrasound transducers of an ultrasound probe (or from an associated signal pre-processing unit) and to process the received signal data for output to an image processing unit for instance. Alternatively, the method may be implemented 'off-line', in isolation from ultrasound imaging apparatus itself, for instance applied at a later time, after data capture has already occurred.

As will be well-known to the skilled person, ultrasound signals may be applied to a body to be imaged, typically directed along a single 'line' or path through the body at any one time, for instance by a transducer array coupled to an ultrasound probe. The applied ultrasound stimuli are partially back-reflected at each boundary encountered as the signals pass through the body, leading to receipt at the transducer array of a series of echo back-reflections, received from different depths within the body. The time intervals between the different peaks in the echo-signals may be used to determine relative distanced between different medium boundaries in the body, from which a visual representation of the body may ultimately be constructed. Although the initially applied ultrasound pulse signal may be relatively short in duration, the resulting echo signal will typically be more temporally extended, as it will contain echo pulses received from a plurality of different depths within the imaged body and at different times depending upon the depth.

As the skilled person will be aware, the echo signal received back at the transducer array in response to application of the ultrasound stimulus is commonly referred to in the art as the RF signal or RF data. RF signal is therefore a term of the art, and is not to be confused with the literal concept of radio frequency signals. The term may be used in the present disclosure to refer to the raw ultrasound signal data.

Embodiments of the invention are based on application of persistence to the ultrasound echo signal data in a raw state; that is, in advance of any envelope-extraction. Such data may be the raw RF signal data, but may also be a complex IQ representation of the signal data and/or baseband IQ data. Any reference to RF data specifically should not be construed as limiting, and should be understood as replaceable by any other form of raw signal data (such as IQ data) without affecting the functioning of the described embodiment. The raw data may also be either fully sampled or down-sampled raw signal data.

Embodiments of the invention are based on applying coherent averaging (coherent persistence) to RF echo signals corresponding to the same path or section through a body at a series of successive times. For brevity, in the present disclosure such RF signals of the same path/section at successive times will be referred to as 'RF frames'. A single RF frame therefore refers to a data representation of one or more RF echo signals representative of a single path or section (i.e. plane) or volume through a body at a substantially singular time (or time interval). Where a frame is representative of a section or volume, the data representation may contain signal data corresponding to a plurality of individual adjacent paths forming said section.

A series of echo signal representations corresponding to that same path or section at a plurality of consecutive time (intervals) may be referred to as a series of RF frames. The term 'frame' in this context is intended merely to capture the temporally consecutive nature of the echo signals, and should not be confused with the concept of an 'image frame' which refers to data processed such as to form a visual or graphical image.

Coherent averaging or persistence in the present context means averaging or persistence applied to raw signal data or frames. Incoherent averaging or persistence in the present disclosure refers to averaging or persistence applied to envelope extracted data or ultrasound images. Furthermore, in the present disclosure, the terms image-based or envelope-based (incoherent) persistence are used to refer to persistence operated on both envelope data and persistence operated on data after logarithmic compression. The term RF-based persistence may be used interchangeably for coherent persistence, whether the persistence really uses RF data, IQ data or baseband IQ data. Results described in the present disclosure were primarily obtained from baseband IQ data at 5 MHz sampling.

As discussed above, coherent persistence (that applied to raw signal data) achieves better signal-to-noise (SNR) improvement than incoherent persistence (that applied to envelope data or images).

To quantitatively compare the difference between the SNR gain of coherent and incoherent persistence or averaging, a simple signal model will briefly be discussed enabling calculation of SNR. Let $s_k = S + n_k$ denote a (noise-corrupted) RF signal of RF frame k, where S is a constant representing the true signal, and $n_k$ complex zero-mean Gaussian noise of unity power. Without loss of generality, S is assumed real. The single-frame power SNR is therefore $S^2$. The power SNR after averaging K RF frames is $$SNR_{RF,K} \stackrel{def}{=} \frac{\text{signal power}}{\text{total power} - \text{signal power}} = \frac{S^2}{E\left\{\left|\frac{1}{K}\sum_{K=1}^{K}(S+n_k)\right|^2\right\} - S^2} =$$

$$\frac{S^2}{\left[S^2 + \frac{1}{K^2}E\left\{\left|\sum_{K=1}^{K}n_k\right|^2\right\}\right] - S^2} = \frac{S^2}{\left[S^2 + \frac{1}{K^2}K\right] - S^2} = KS^2$$

where E is the expectation operator.

Note that in the above denominator, since $n_k$ is a random noise of unity power, its sum over K frames adds to $\sqrt{K}$. Hence $E\{|\Sigma_{K=1}^{K} n_k|^2\} = |\sqrt{K}|^2 = K$.

In this case, the SNR increase from averaging is K. Converting to decibels using the well-known formula SNR=10 $\log_{10}$(SNR) dB, the SNR gain is equal to 10 $\log_{10}$K dB.

The power SNR in the case of averaging over K envelope frames (i.e. incoherent averaging) is given by $$SNR_{envelope,K} \stackrel{def}{=} \frac{\text{signal power}}{\text{total power} - \text{signal power}} = \frac{S^2}{E\left\{\left(\frac{1}{K}\sum_{K=1}^{K}|S+n_k|\right)^2\right\} - S^2}$$

FIGS. 1(a) and (c) show plots comparing numerical results for coherent and incoherent persistence in terms of resulting SNR (y-axis; dB) per number of frames averaged (x-axis), where each single frame has an SNR of 3 dB in FIG. 1(a) and 20 dB in FIG. 1(c). The upper curve in each plot corresponds to the SNR change for coherent (RF-frame) persistence, while the lower curve shows the SNR change for incoherent (envelope-frame) persistence. FIG. 1(b) and FIG. 1(d) show the difference in the resulting SNR (y-axis; dB) between coherent and incoherent averaging per number of frames averaged (x-axis) for each of the plots of FIG. 1(a) and FIG. 1(c) respectively.

The curves show superior SNR improvement performance of RF-based persistence compared to envelope-based persistence. One source of this difference may be the fact that averaging over envelope frames cannot reduce noise-introduced signal-level-dependent bias in amplitude and therefore it is not effective in revealing the true signal amplitude, as opposed to RF-based averaging.

The above model and sample results show that coherent (raw or RF signal based) persistence or averaging gives superior improvement in SNR compared to incoherent (envelope-signal) based persistence.

The above-demonstrated improvement of SNR by coherent summation of data assumes that the collected signal representations maintain spatial coherence between the RF-frames to be averaged. However, when imaging tissue in vivo rather than a static phantom, relative motion between the ultrasound transducer and the body being imaged, if not managed properly, can degrade spatial coherence and result in deterioration in performance. The impact of motion increases in relation to the number of frames averaged in the persistence operation. This means that for coherent averaging, typically only very small averaging kernels can be used in order to avoid significant breakdown in spatial coherence between averaged RF frames and therefore deterioration in SNR improvement.

However, to circumvent this, and enable larger averaging kernels, in accordance with embodiments of the present invention, the raw RF signal frames are first pre-processed with a motion compensation procedure in advance of application of persistence in order to mitigate any spatial incoherence introduced by relative motion of the body being imaged. This ensures that, upon averaging over multiple frames as part of the coherent persistence, motion artifacts introduced by destructive interference (arising by averaging non-aligned RF signals) is avoided.

Optionally, a combination of motion-compensated RF persistence and subsequently applied standard incoherent persistence may be used.

Simple example implementation of coherent persistence will now be described, before moving on to explain application of this within embodiments of the present invention.

For coherent persistence, when averaging over K frames, the incremental gain of SNR for each extra frame averaged is most pronounced when K is small. This is evident in FIGS. 1(a) and (c) which show a logarithmic-like relationship between cumulative SNR and number of frames averaged. This suggests that the most pronounced gains in SNR from coherent persistence may be achieved at the very start of the persistence process. For this reason, it is desirable to apply coherent persistence at least over an initial few RF frames, even if not over all frames, so that a few dB of SNR gain can be easily achieved.

One of the simplest forms of RF-based persistence is direct low-pass filtering, for example applied to beam-summed (i.e. beamformed) RF signal data over multiple 'frames', i.e. filtering a series of signals representative of different times or different time periods (or filtering 'in slow time' as it is often referred to in the art).

Figure 2:
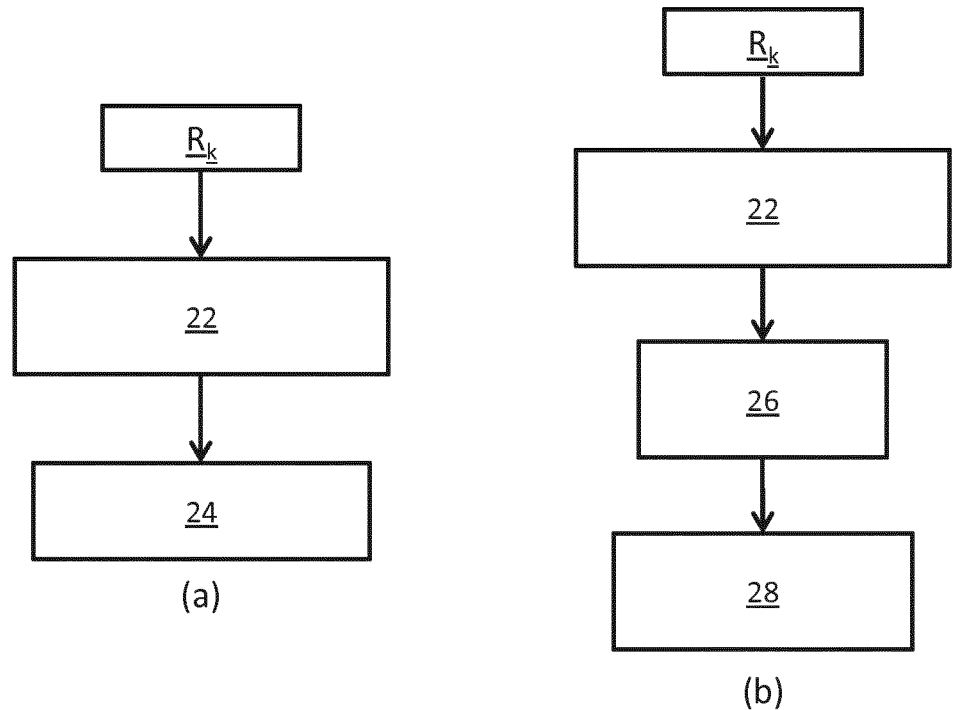
FIG. 2 shows block diagrams illustrating example coherent persistence processes in the absence of motion compensation.

The low pass filter may for instance be a simple as a moving average filter. An example process incorporating such persistence is shown in FIG. 2(a) wherein K RF frames $R_k$ are passed through a low pass filter in step 22, thereby producing filtered RF frames. The filtered RF frames are then post processed in step 24, for instance through envelope-extraction and/or image generation.

In more complex examples, the simple coherent persistence 22 may be followed by a subsequent step of image-based persistence. FIG. 2(b) shows an example, wherein K RF frames $R_k$ are first passed through a moving average filter in step 22 to produce K filtered RF frames. The frames are then processed in step 26 with frequency compounding.

Frequency compounding is a well-known procedure in the art. In brief, frequency compounding comprises the following steps. The raw RF data is independently filtered M times, each with a different bandpass filter. The bandpass filters differ in bandwidth and central frequency. These M separate filtration processes produce a set of M envelope datasets or images, each differing slightly, in particular in terms of their speckle since this is frequency dependent. Those M envelope datasets or images are then combined (i.e. averaged) incoherently.

Since different RF frequencies within the raw data are expected to result in different realizations of the speckle, the process of incoherently averaging the M differently filtered datasets has the effect of averaging the speckle, thus lowering speckle variance and increasing image quality.

Frequency compounding is not essential to the invention, and merely represents one example of a procedure that may be applied to the K filtered RF frames.

Following this, the data is processed to form one or more images, and image-based (incoherent) persistence applied in step 28. This is hence an example of a 'hybrid' approach in which both coherent and incoherent persistence are used.

Although frequency compounding is shown in the example of FIG. 2(b), this is by way of mere illustration only and is not essential to any persistence process used in embodiments of the present invention.

Figure 3:
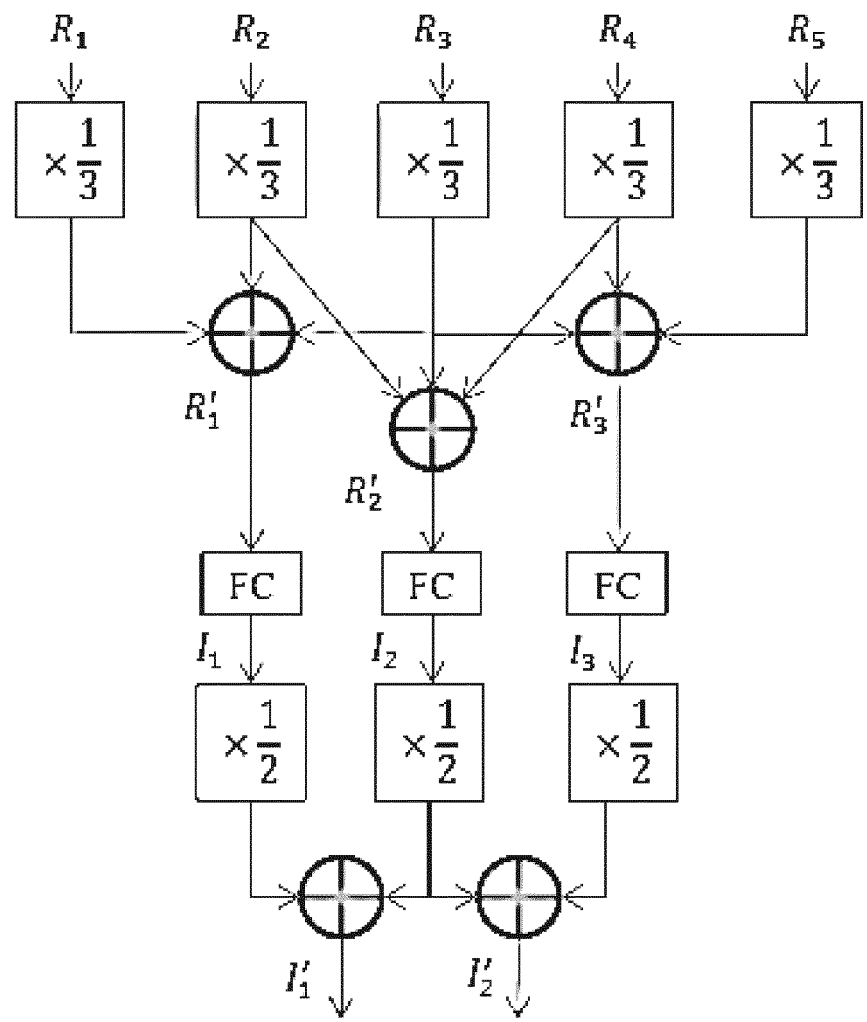
FIG. 3 shows a flow diagram illustrating an example coherent persistence process in the absence of motion compensation.

FIG. 3 shows in schematic flow-diagram form the procedure applied in FIG. 2(b). The procedure is applied to an initial input series of five RF signal frames $R_n$. A persistence process is applied consisting of application of a moving-average calculation procedure (via a moving average filter). As shown, this results in generation from the five input RF frames of three averaged frames $R_n'$, each formed from an average of three of the input frames. For instance $R_1$, $R_2$ and $R_3$ are each multiplied by ⅓ and then summed to form $R'_1$.

Each of the three averaged RF frames is then processed with frequency compounding (abbreviated as FC in FIG. 3). Following this, the RF signal frames are processed to form either envelope frames or image frames $I_1$, $I_2$, $I_3$ and then a persistence process applied to the envelope or image frames to achieve average envelope or image frames $I'_1$ and $I'_2$. In the example shown in FIG. 3, the image-based persistence process comprises simply application of a moving-average procedure, wherein each of averaged image frames $I'_1$ and $I'_2$ are formed of an average of two of the frequency compounded image frames $I_1$, $I_2$, $I_3$.

The above discussion has illustrated some simple examples of coherent persistence as may be included as part of embodiments of the invention.

However, such methods applied on their own would rely on operators of ultrasound imaging probes keeping the probes extremely still so as to manually minimize motion artifacts. On their own, the above procedures might be suitable for improving SNR over very short series' of signal frames (so called 'weak' persistence), where the risk of movement between frames within the body being imaged is less. However, even here, in the presence of local motion of physiological features or structures within the body, it might even be hard to maintain coherence between directly consecutive frames.

To allow for a larger RF persistence kernel (i.e. a larger series of averaged RF frames) and to enhance robustness against physiological motion, motion compensation is, in accordance with embodiments of the invention, incorporated to register, or align, RF frames with respect to each other before averaging.

The number of RF frames to be included in each averaging kernel (i.e. to be included in each averaged signal) can be adaptively determined in accordance with some examples, by a confidence measure that is derived during motion compensation.

Figure 4:
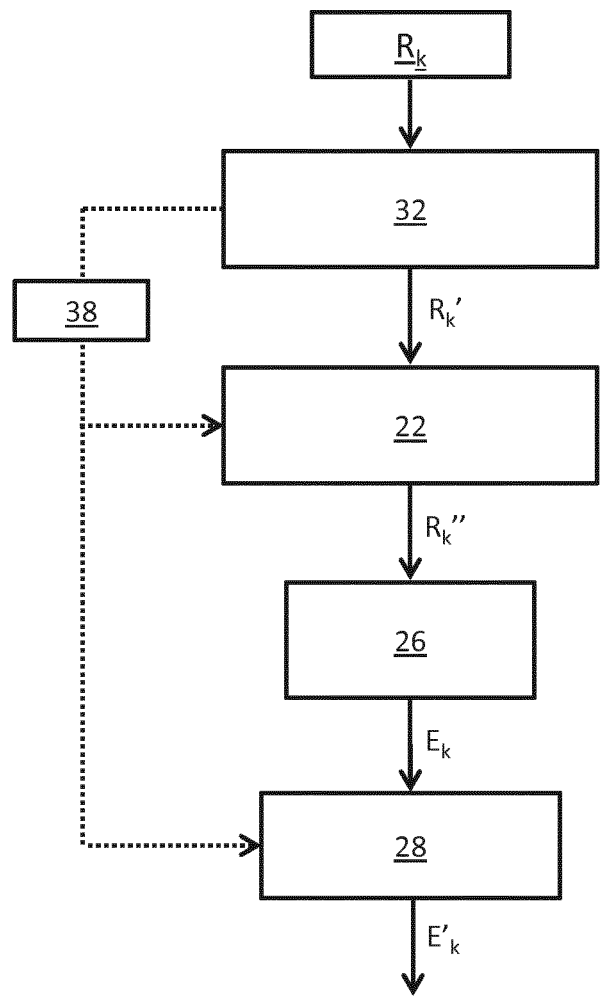
FIG. 4 shows an example method in accordance with an embodiment of the invention, wherein a combination of coherent and incoherent persistence is applied.

One example of a method in accordance with an embodiment of the invention is illustrated in FIG. 4.

A series of K RF frames $R_k$ are received and are first processed in step 32 in accordance with a motion estimation and compensation procedure in order to reduce motion-induced deviations or displacements between the respective frames of the series and thereby register the RF frames to one another. A phase correction procedure is also applied. Following this, a coherent persistence procedure 22 is applied to the resulting motion-compensated frames $R_k'$. The persistence procedure may for instance simply comprise a moving average of the frames (in in the example of FIG. 3) or may comprise a weighted average. The weightings may be derived based on an estimated degree of alignment or spatial coherence of each frame to all of the other frames. This will be described in greater detail below.

The coherent persistence or averaging procedure 22 results in a set of motion compensated, averaged RF frames $R''_k$. These may then be processed in step 26 with frequency compounding to realize K equivalent envelope frames $E_k$ comprising envelope extracted ultrasound signal data. Following this, the envelope frames may be processed in step 28 with non-coherent persistence, wherein an averaging procedure is applied to the envelope frames, resulting in a set of averaged envelope frames $E'_k$.

Optionally, during motion tracking, an extra step 38 may be performed to derive a confidence measure regarding how well the registration between different RF frames has been performed in step 32. A candidate for this confidence measure may be the cross-correlation coefficient among registered RF frames $R'_k$. Based on the confidence measure, the optimal RF persistence kernel size (i.e. the optimal number of frames to be averaged) can be determined. The registration results can also be used to decide on the kernel size for the envelope-based persistence operation executed subsequently. Where the confidence measure is low, meaning the RF frames are not well registered, the size of the averaging kernel may be selected to be small, so as to minimize the risk of motion-induced artifacts in the averaged frames $R''_k$ and/or $E'_k$.

Although in the example of FIG. 4, the motion estimation and compensation step 32 and the coherent RF persistence step 22 are shown as separate, in alternative examples, they may be coupled or integrated into one single operation or method step. In step 32, motion estimation and compensation is performed on the raw RF frames. Many suitable algorithms exist for estimating motion, including standard Doppler processing (1-D), speckle tracking between RF frames, cross-correlation, or a sum of absolute difference procedure (2-D or 3-D). Speckle tracking is a well-known method in the present field and the skilled person would be aware of means for applying it. Tracking of movement between frames may also be determined based on gradient descent or optical flow.

Gradient descent and optical flow are iterative optimization techniques that aim to find the deformation or displacement field between RF frames that minimizes the difference of intensity values between a reference frame and a frame which is warped to the reference frame. See for instance O. Somophone, "Fast Myocardial Motion and Strain Estimation in 3D Cardiac Ultrasound", 2013.

Tracking motion with higher dimensional data is also an option. For example, in the case of 2-D imaging, better robustness against noise or interference can be achieved by using 2-D tracking with 3-D (2-D spatially plus 1-D temporally) data, especially at deeper imaging depths within the body where signal-to-noise ratio is typically low to begin with. Motion tracking with four dimensional data can also be performed (i.e. 3-D spatially, plus 1-D temporally).

As an alternative to directly registering the RF frames to one another, one efficient approach is to instead apply a two-step method comprising first determining deviation or displacement between the corresponding envelope signals for the frames, and then subsequently applying these determined deviations to the original raw RF frames in order to warp the frames to one another and achieve registration. Displacement estimation between envelope signals is a well-known task in ultrasound imaging. One particularly fast and efficient algorithm for achieving this, in particular in the case of real-time signal analysis and imaging, is the "Spare Demons" tracking algorithm. This is described in detail for instance in O. Somphone, "Fast Myocardial Motion and Strain Estimation in 3D Cardiac Ultrasound", 2013.

The algorithm takes as input the corresponding envelope signal representations/frames $E_0$, $E_1$ of at least two RF signal frames $R_0$, $R_1$. These are derived for instance by taking a copy of the RF signal frames and then applying a procedure to extract the envelope data, from which corresponding envelope frames may be constructed. One of the envelope signal frames $E_0$ is denoted as a 'reference' frame and the other $E_1$ as a 'template' frame.

An estimated displacement (or displacement 'field') is determined between the reference frame $E_0$ and the template frame $E_1$. This displacement corresponds to motion of the body being imaged between the successive frames.

Once the displacement field between the reference envelope frame and template envelope frame is calculated, this may then be added or otherwise applied to corresponding original RF template frame so as to register the RF template frame to the RF reference frame. This process is known as 'warping' the template frame to the reference frame.

Once the template frame has been registered or warped to the reference frame, the phase of the template frame must, for this embodiment, be compensated to align with that of the reference frame. A residual phase between the two frames is calculated, and the phase of the template frame adjusted accordingly.

The process may be represented in equations as follows. Consider two RF signal frames $R_0$, $R_1$ to be registered to one another. First, the corresponding envelope-signal representations or frames $E_0$, $E_1$ are extracted (representing variation of amplitude of the RF signals).

The task is to register $R_1$ to $R_0$.

Displacement estimation is first performed between the envelope frames $E_0$ and $E_1$. The problem of displacement estimation is to find the motion field $u(x)$ that minimizes $$E\{|E_0(x)-E_1(x+u(x))|^2\}$$

Any appropriate technique may be performed to find the displacement field $u(x)$, including for instance optical flow, gradient descent, or any other technique. Note that so far only the envelopes have been used.

Based on the displacement field $u(x)$, the RF frame $R_1$ must be warped to the reference RF frame $R_0$.

Warping the RF data is performed by interpolating the frame $R_1$ as follows:

$$R_{1_{warp}}(x)=R_1(x+u(x))$$

Note that this operation applies to the RF (i.e. raw) data. Following this, residual phase between $R_0$ and $R_1$ is compensated. The residual phase $\alpha(x)$ may be determined as follows:

$$\alpha(x)=\text{angle}(E\{R_0(x)R_{1_{warp}}(x)^*\}$$

The phase compensation of $R_1$ to match $R_0$ may then be performed as follows:

$$R_{1_{warp\_phase\,compensated}}(x) = R_{1_{warp}}(x)e^{i\alpha(x)}$$

Now $R_0$ and $R_{1\_warp\_phase\,compensated}$ can be summed (coherent summing) and a coherent average subsequently derived (coherent persistence). Their structures will align (based on the warping with $u(x)$) and their phases will be aligned (based on the phase compensation).

Examples of procedures for reducing deviation between an entire series of RF frames (i.e. registering a series of RF frames) will now be described in detail.

Embodiments of the invention are based on the concept of applying persistence to a consecutive series of echo signal frames after application of motion compensation. In applying motion compensation to such a series of frames, it is desired that all frames should be aligned (or registered) to one another. One efficient approach to achieving this is to designate a single frame in the series as a reference frame and to determine a deviation between every other frame and this reference frame in respect of certain features or characteristics. Each frame is then warped or adjusted in accordance with its respective determined deviation from the reference frame such as to eliminate the deviation and render it better aligned or cohered with the reference frame. Warping each frame according to a deviation with the same single reference frame, rather than for instance with respect to an adjacent frame, has been found to be more accurate, since the deviation tends to be greater for more temporally disparate frames, and hence the margin of error in its determination less.

Although in preferred examples a deviation between each frame and a reference frame is ultimately determined, this may, in accordance with one or more examples, be derived through an algorithm that is based upon determining deviations between consecutive frames, and then appropriately summing these in order to determine deviations between each frame and the reference frame.

Figure 5:
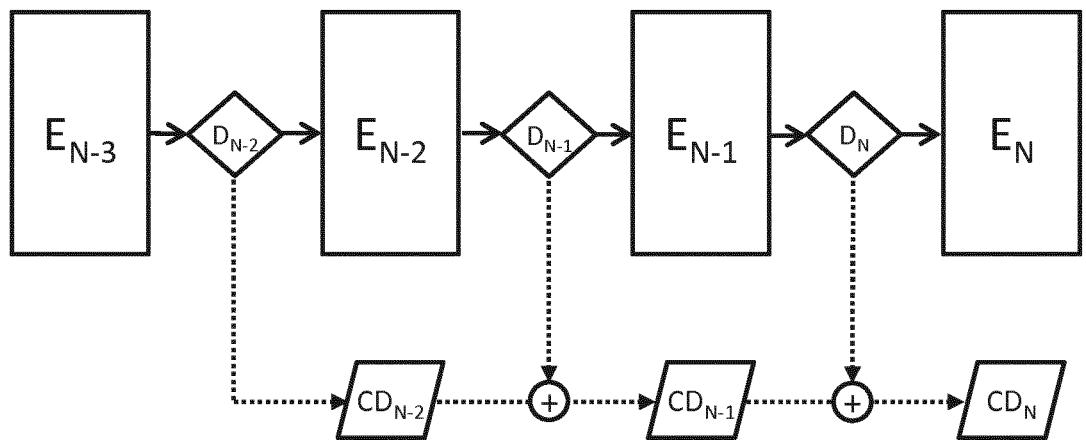
FIGS. 5-7 schematically illustrate in flow diagram form an example motion compensation algorithm as incorporated within one or more embodiments of the present invention.
Figure 6:
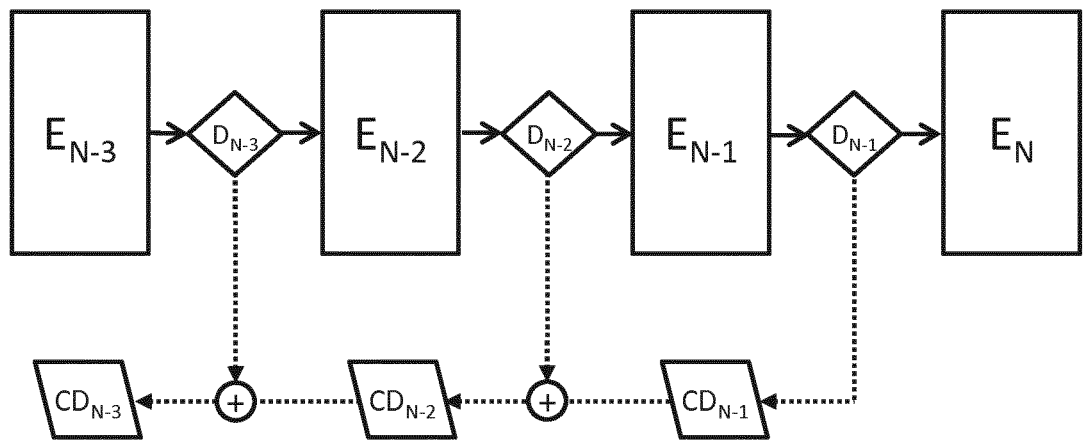

Examples of this approach are illustrated in FIGS. 5 and 6. In this example, as in the example described above, registration is performed by first determining deviations between the corresponding envelope-signal frames for a series of RF frames, and then adjusting the RF frames in accordance with these determined envelope frame deviations. FIGS. 5 and 6 illustrate the process of determining the deviations between the envelope-signal frames $E_n$ corresponding to the series of raw RF frames. The figures show the series of envelope frames $E_n$, the inter-frame deviations D between consecutive frames, and the cumulative deviations CD between each of the frames and one of the frames designated as a reference frame.

In accordance with a first approach, illustrated in FIG. 5, the reference frame may be designated as the temporally first envelope-signal frame in the series. In the case illustrated, this is envelope-signal frame $E_{N-3}$. The deviations $D_n$ between each consecutive pair of envelope-signal frames is determined. Following this, these deviations are successively summed so as to provide a respective cumulative deviation $CD_n$ for each signal frame apart from the reference frame $E_{N-3}$. These indicate a total deviation between each frame $E_n$ and the reference frame.

As shown, the first cumulative deviation $CD_{N-2}$ for frame $E_{N-2}$ consists simply of the inter-frame deviation $D_{N-2}$. The cumulative deviation $CD_{N-1}$ for frame $E_{N-1}$ is equal to the sum of inter-frame deviations $D_{N-2}$ and $D_{N-1}$. The cumulative deviation $CD_N$ for frame $E_N$ (the most temporally recent frame in the series) is equal to the sum of all three inter-frame deviations $D_{N-2}$, $D_{N-1}$, and $D_N$.

Following determining of the cumulative deviations between each of envelope-signal frames $E_{N-2}$, $E_{N-1}$, $E_N$ and the designated reference frame (temporally first envelope-signal frame $E_{N-3}$), these cumulative deviations are used to warp each of the original raw RF signal frames $R_{N-2}$, $R_{N-1}$, $R_N$ (not shown) to the corresponding reference RF frame $R_{N-3}$ so as to eliminate the deviations. Warping may be achieved in accordance with the procedure outlined above, wherein each RF frame is interpolated based on its respective cumulative deviation or displacement. In other words, $R_{n\ warp}(x) = R_n(x + CD_n(x))$, where $CD_n(x)$ is the cumulative deviation field used to warp the RF frame and x is the grid of sample points (where this may be a time dimension, i.e. t, for a raw RF signal for instance).

In accordance with a second example, schematically depicted in FIG. 6, the most temporally recent envelope-signal frame (in the case illustrated, $E_N$) is designated as the reference frame. As in the example of FIG. 5, inter-frame deviations $D_{N-1}$, $D_{N-2}$ and $D_{N-3}$ are determined between each consecutive pair of envelope-signal frames. Following this, a set of cumulative deviations $CD_N$ are calculated, this time starting from the most recent frame $E_N$ and working backwards to the first signal frame $E_{N-3}$. Each of the cumulative deviations $CD_N$ thereby gives a total deviation between each of the frames $E_{N-1}$, $E_{N-2}$ and $E_{N-3}$ and the reference frame $E_N$.

Again, once the cumulative deviations are calculated, each of the corresponding original raw RF frames $R_{N-1}$, $R_{N-2}$ and $R_{N-3}$ may be warped to the designated reference RF frame $R_N$ based on the envelope deviations in the manner described above.

In accordance with either of the above approaches (of FIG. 5 or FIG. 6), calculation of the inter-frame deviations $D_{N+1}$ and/or the cumulative deviations $CD_n$ may be performed all at once, for instance after collection of all frames which are to be included in the series. Alternatively, the inter-frame deviations and cumulative deviations may be determined 'in real time', such that these are appended and/or updated each time a new signal frame is added to the series.

In accordance with the example of FIG. 5, this would require, upon appending of each new frame RF frame $R_n$, determination of the corresponding envelope frame $E_n$ and then calculation of the intra-frame deviation between said envelope frame and the immediately preceding envelope frame $E_{n-1}$. It would then require calculation of a cumulative deviation for the appended envelope frame with respect to the reference envelope frame (in this case $E_{N-3}$). This would simply require adding the newly determined inter-frame deviation $D_{n+1}$ to the previous three inter-frame deviations, or equivalently, to the immediately preceding cumulative deviation $CD_n$. This process would be repeated for each new frame appended to the series. The newly updated deviations may then be reapplied to the corresponding series of original raw RF frames to achieve motion compensation.

In accordance with the example of FIG. 6, 'real time' calculation of the deviations would be more complex, requiring updating of all previously calculated cumulative deviations. This is because in the example of FIG. 6, the reference frame is designated as the most recent frame. Hence, if a new frame is added, the reference frame has changed and previously calculated cumulative deviations are no longer accurate. However, the example of FIG. 6 may be preferred, despite the possible slight additional computational cost, since it reduces apparent 'time lag' in subsequently generated images. Since all RF frames are warped to the temporally most recent frame, the resulting average provides a representation of the imaged body at the time of the most recently captured signal, rather than a time, say two or three frames in the past.

Figure 7:
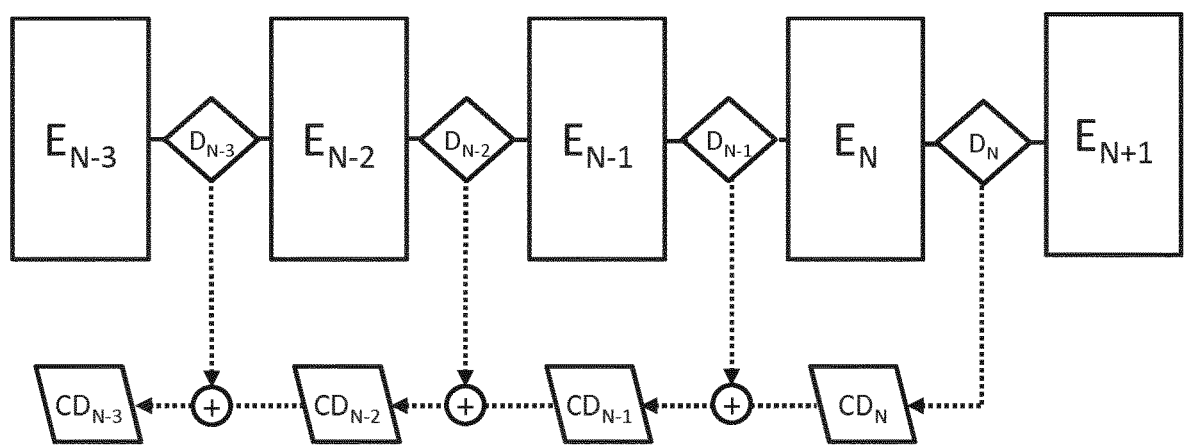

For the example of FIG. 6, upon appending of a newly acquired RF frame $R_{N+1}$, new envelope frame $E_{N+1}$ is extracted. The inter-frame deviation $D_N$ between this frame and the immediately preceding frame $E_N$ is then calculated. Following this, each of the previously calculated cumulative deviations $CD_{N-3}$, $CD_{N-2}$, and $CD_{N-1}$ must be updated by adding to them the newly calculated inter-frame deviation $D_{N+1}$. This in effect updates all of the cumulative deviations such that they each provide the total deviation between each of the respective envelope frames and the newly added envelope frame $E_{N+1}$. Finally, a new cumulative deviation must be added for frame $E_N$ (which is now no longer the reference frame), this being equal simply to the new inter-frame deviation $D_N$ between new frame $E_{N+1}$ and immediately preceding frame $E_N$. The resulting, updated, frame structure is shown in FIG. 7.

The above described process achieves efficient registering of RF frames to one another so as to align amplitude peaks and reduce the risk of motion artifacts. However, as discussed above, even when the RF frames have been warped or adjusted such that their respective envelopes' features are matched, the RF signals comprised by said frames are not necessarily coherent with one another. Summing them as such when motion has occurred generally results in black stripes and cracks due to destructive interferences.

To eliminate these artifacts, a phase adjustment procedure must also be performed.

In the phase adjustment procedure, the local phase shift at every sample (of each RF signal) of each warped RF frame $f_i$ with respect to the corresponding samples of the designated reference frame $f_0$ is first estimated. The phase shift is then corrected for instance through use of a suitable convolution kernel K. This similar for instance to a Doppler estimation and can be performed for instance on down-sampled IQ data.

To estimate the local phase shift for every RF signal of each RF frame, the following estimation expression may be used:

$$\alpha = \angle (K \otimes (f_0 \cdot f_i^*)) \quad (1)$$

where $f_0$ and $f_i$ are complex representations of the reference and warped RF frames respectively.

Adding the quantity derived from (1) to the warped template's phase ensures constructive interference with the reference, and therefore mitigation or elimination of motion artifacts arising due to phase incoherence:

$$f_i' = f_i \cdot e^{i\alpha} \quad (2)$$

Since this procedure is aimed at remedying spatial displacements between two lines or planes of focus of two respective RF frames using phase adjustment, the procedure only makes sense where the spatial displacement is less than the length of a single pulse wavelength, and ideally under a quarter of a pulse wavelength (half a wavelength in round trip) in the axial direction and under one (A-line) path width in lateral dimension.

Although the warped template and the reference do not necessarily always fulfill these conditions, the resulting average, when the RF data is rendered into an image, still looks relatively sharp and defect free up to a certain inter-frame distance.

The frame warping (amplitude peak adjustment) and phase adjustment may be thought of as two parts of an alignment procedure, operating at different scales, or precision levels. Frame warping aligns the envelope peaks, but leaves errors in the signal alignment on the order of ¼ wavelength. Phase adjustment remedies these residual small-scale misalignments.

Figure 8:
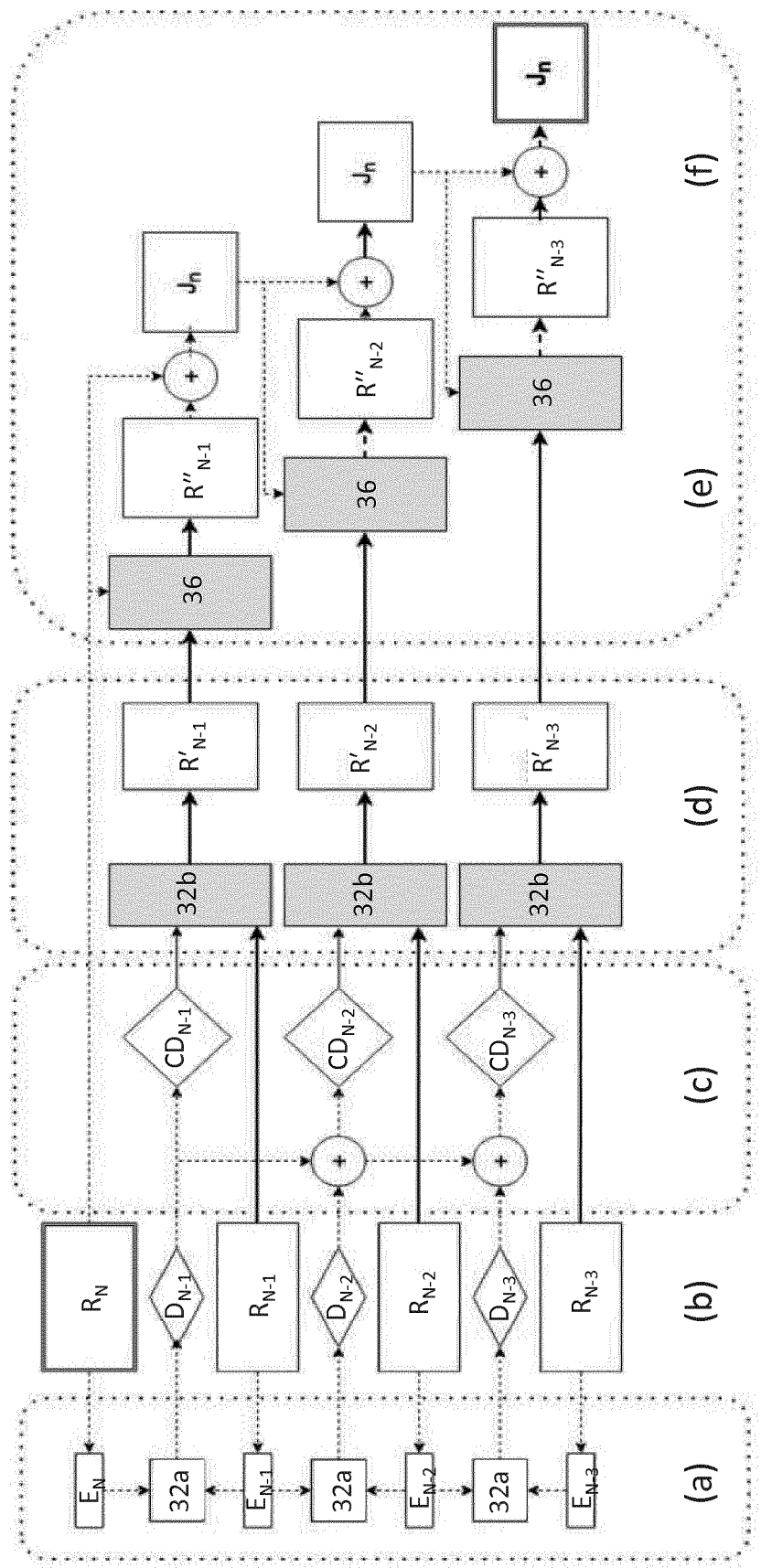
FIG. 8 schematically illustrates an example signal processing method in accordance with an embodiment of the present invention.

FIG. 8 schematically outlines the full procedure for processing a series of RF frames in accordance with an embodiment of the invention. As discussed above, the term RF frame in the present disclosure is used by way of shorthand to denote a data representation of one or more raw (RF) echo signals representative of a given path or section through a body being imaged at a particular time. The series of RF frames represent said same path or section through the body at a series of respective time points. Each RF frame may comprise data representative of multiple adjacent paths (or multiple 'lines') forming a section through the body.

In the example processing method of FIG. 8, a series of four RF frames, $R_n$ (shown at (b)), are applied first with a motion compensation procedure (stages (a)-(d)), then a phase correction procedure (stage (e)) and then finally a summing and averaging procedure (stage (f)).

In accordance with a first stage (a), each RF frame $R_n$ is processed to extract a corresponding envelope signal $E_n$. As in the motion tracking procedure described above with reference to FIGS. 5-7, once the envelope data has been extracted, consecutive, inter-frame deviations $D_n$ between each neighboring pair of envelope frames $E_n$ is then calculated (in step 32a).

One of the RF frames $R_n$ (and corresponding envelope frame $E_n$) is designated as a reference frame. In this case, the reference frame is designated to be $R_N$ (and $E_N$) (the top frame shown in FIG. 8). Once the consecutive, inter-frame deviations have been determined, cumulative deviation $CD_n$ are calculated (in stage (c)) giving the total deviation between each envelope frame $E_n$ and the reference envelope frame $E_N$. These are generated (as shown in step (c)) by successively summing the inter-frame consecutive deviations $D_n$ previously calculated, starting from $D_{N-1}$ and continuing downwards to $D_{N-3}$. The result of this is a set of three cumulative deviations, $CD_{N-1}$, $CD_{N-2}$, and $CD_{N-3}$ corresponding respectively to the total deviation between the each of envelope frames $E_{N-1}$, $E_{N-2}$, and $E_{N-3}$ and the reference envelope frame $E_N$.

Following calculation of the cumulative deviations $CD_n$, in stage (d), each of the original, raw RF frames $R_n$ (excluding the reference frame $R_N$) is warped or adjusted to the reference frame, based on the calculated cumulative deviations between the envelope frames $E_n$. This warping (or adjusting) procedure is shown as step 32b, and generates as output a set of warped RF frames $R'_n$ corresponding to each of RF frames $R_{N-1}$, $R_{N-1}$, $R_{N-1}$ warped to the reference frame $R_N$ to substantially eliminate the calculated deviations $CD_n$.

Following generation of the warped RF frames $R'_n$, in stage (e), a phase correction procedure 36 is then applied (for example, as outlined in more detail above) so as to adjust the phases of each of the warped RF frames to align with that of the reference frame $R_N$. The output of the phase correction procedure 36 is a set of three fully motion-compensated RF frames $R''_n$.

Finally, in stage (f), the motion compensated RF frames $R''_n$ are each added to the reference frame, to form a coherent sum $J_n$ of reference frames. A coherent average may be derived simply by applying a relevant weighting factor to each of the motion compensated frames $R''_n$ before summing.

Preferably, the above process is done in a stepwise manner, wherein each and every stage ((a)-(f)) of the process is performed for a given frame, before moving on to the next frame and repeating the process Advantageously, this allows new frames to be added to the series, and for the process to be easily updated to accommodate the new frame. With each frame for which the process (stages (a)-(f)) is performed, the resulting motion compensated frame $R''_n$ is added to a running partial sum $J_n$, representing a sum of all compensated frames so far calculated (or indeed, so far received).

Where this step-wise approach is followed, preferably, in the phase correction stage (e), the phase adjustment of each warped frame $R'_n$ is performed 'indirectly', with respect to the phase of the partial sum $J_n$, rather than with respect to the reference frame $R_N$. This ensures that coherence is maintained at all stages of the procedure. However, direct phase adjustment with respect to the reference frame may alternatively be performed.

It is also possible, similarly, to perform the frame warping of each successive RF frame $R_n$ to the coherent running average $J_n$, rather than to a particular reference frame. In this case cumulative deviations are calculated between each frame and the latest partial sum $J_n$.

The advantage in the above procedure of FIG. 8 of calculating first the inter-frame deviations $D_n$ and then the cumulative deviations $CD_n$ (between each frame and the reference frame) is that the resulting algorithm is more efficient for application to real-time data processing where additional new RF frames are repeatedly appended to the series. By way of example, for each new frame $R_{n+1}$ added to the series, the following steps may be performed, to update each of the motion and phase compensated frames and update the averaging sum $J_n$.

New RF frame $R_{N+1}$ is received.

This frame is designated as the new reference frame.

This frame is processed to extract the envelope-signal to form corresponding envelope signal frame $E_{N+1}$.

The inter-frame displacement $D_N$ is calculated between the new envelope frame $E_{N+1}$ and envelope frame $E_N$.

This new inter-frame displacement $D_N$ is added to every existing cumulative displacement $CD_n$ (that is, to each of $CD_{N-1}, CD_{N-2}, CD_{N-3}$). The result is a set of new cumulative displacements giving the displacement between each frame and new frame $R_{N+1}$. Each of frames $R_N$ to $R_{N-3}$ is warped 32b to the new reference frame $R_{N+1}$ based on the updated cumulative deviations.

The warped frames are each re-processed 36 to correct any phase difference with respect to the newly added frame.

The coherent sum $J_n$ is recalculated by summing each of the new warped, phase-adjusted frames Angle correction (phase adjustment) 36 is required regardless of the number of frames included in the coherent sum or average $J_n$, in order that motion artifacts be effectively reduced. As noted above, to maintain coherence at every stage of the summation (stage (f)), preferably the angle correction 36 is applied with respect to the phase of the partial summation $J_n$, rather than directly with respect to the reference frame. However, this is not essential, and the alternative is also possible.

Assuming approximately 2 cm/s lateral velocity (of the body being imaged), and a frame rate of 85 captured frames per second, the above method is able to achieve up to 5 frames of persistence (i.e. an averaging Kernel of length five frames). This corresponds to a theoretical signal-to-noise ratio (SNR) increase of approximately 7 dB.

In accordance with one or more embodiments, a hybrid coherent-incoherent persistence method may be performed, wherein the above procedure of FIG. 8 is performed upon each of a plurality of subseries of RF frames, to thereby generate a plurality of coherently averaged RF frames. This plurality of averaged frames may then be processed to extract corresponding envelope frames, and these envelopes then (incoherently) averaged to thereby derive a final hybrid coherent-incoherent averaged signal frame.

In accordance with one or more embodiments of the presently claimed data processing method, the length of the averaging kernel for the persistence process (i.e. the number of RF frames included in the average) may be dynamically adapted in accordance with one or more factors to improve results (as outlined below).

According to an existing approach for partially countering the effects of motion in persistence (where true motion compensation is not applied), the impact of the motion upon the obtained signal data is first assessed (for instance by checking cross-correlation values between the frames), and the length of the persistence (averaging) kernel is then shortened accordingly. For example, where it is determined that correlation between signal frames is low, the averaging kernel may be reduced in size so as to mitigate the risk of introducing motion artifacts. This helps to ensure artifact-free images, while still achieving relatively high SNR for steady observations. (Of course, this comes at the cost of reducing the effectiveness of the persistence process at reducing noise for non-steady observations).

This approach may be advantageously incorporated into embodiments of the present invention (in which true motion compensation is performed) so as to reduce the risk of motion artifacts caused by still imperfect motion compensation. Here, the similarly between each warped frame (termed a 'template frame' for the following discussion) and the reference frame can be measured, and the warped frame may be added to the coherent average only if the similarity is great enough.

Alternatively, the measured similarity may be used to determine a weighting factor for applying the template frame within the final average. For example, a poorly correlated warped template would be given a low weighting. Weightings may similarly be determined and applied to every frame added to the average, so as to realize a resulting average in which motion artifacts are minimized.

Figure 9:
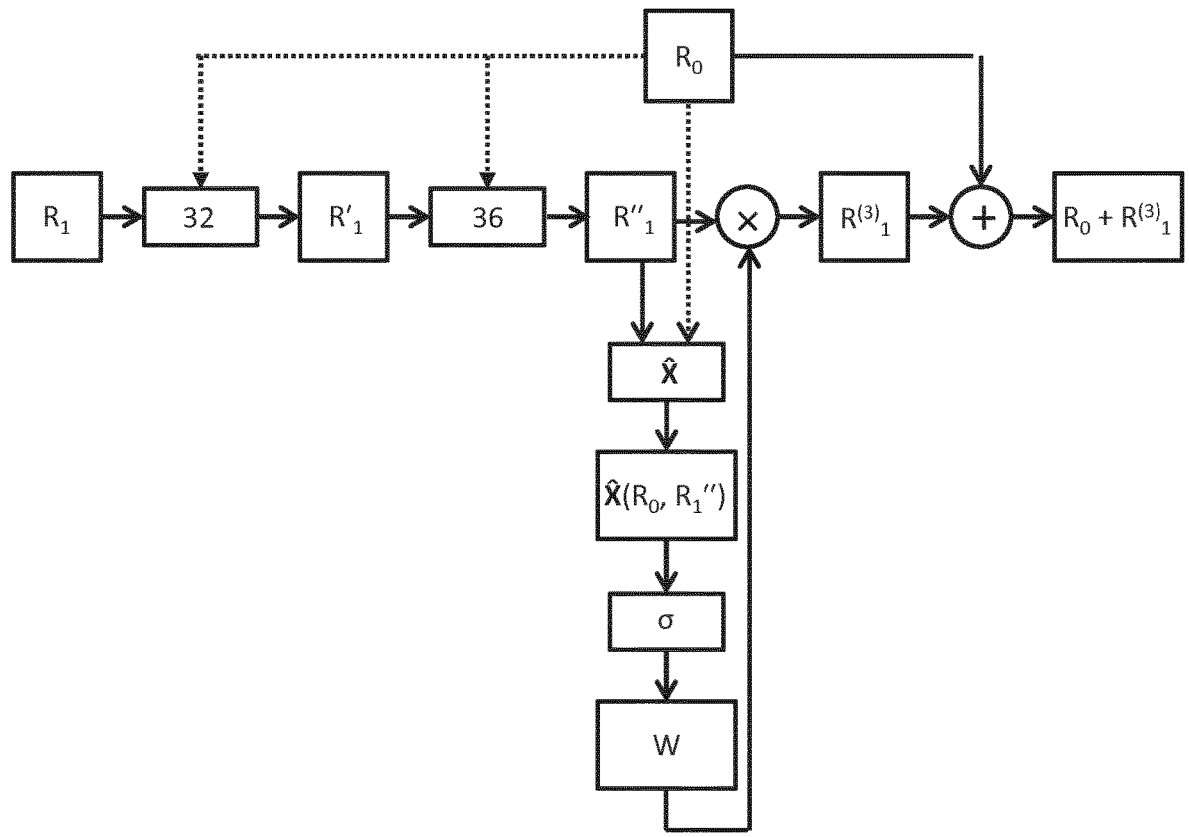
FIG. 9 schematically illustrates an example signal processing method in accordance with the invention in which a weighted average is calculated based on determining similarity metrics.

An example of such a process is illustrated schematically in block diagram form in FIG. 9. Here, motion tracking and compensation 32 with respect to a reference frame $R_0$ is first applied to template frame to realize warped frame $R'_1$, and subsequently, phase adjustment 36 is performed with respect to reference frame $R_0$ to realize fully motion compensated frame $R''_1$. A similarity operation $\hat{X}$ is then applied to determine a similarity measure $\sigma$ between $R_0$ and $R'_1$. Based on this similarity measure, a weighting W is derived for multiplication with frame $R''_1$ in order thereby to derive weighted frame $R^{(3)}_1$. The weighted frame is then added to the final sum. By applying this process to each frame to be added to the sum, good results in terms of reducing motion artifacts may be achieved since strongly non-correlated frames are dampened in terms of their effect within the average.

It is noted that a simple (motion-compensated) average consisting of just two consecutive frames is in most cases unlikely to lead to any significant motion artifacts, even where cross-correlation is relatively low. Hence, for improved computational efficiency, the similarity between the first two frames in any series to be averaged may, in accordance with examples, be ignored. Ignoring this metric only for the second frame should not degrade the resulting images. By contrast, applying a low weighting value to the second frame (where the similarity metric was low) would in fact cause significant drops in the achieved SNR improvement.

In addition to motion, signal noise may also contribute to poor frame correlation. Noise levels generally increase with depth of tissue imaged. Hence, the cross-correlation matrix applied for realizing similarity between two frames may, in accordance with one or more examples, be normalized in accordance with imaging depth in advance of computing the weights W.

In accordance with examples, where a hybrid mix of coherent and incoherent averaging is used (as discussed above), the cross-correlation metric between motion-compensated RF frames may be calculated and used to inform a determination as to how many frames should be coherently and incoherently averaged respectively. Also, different metrics (e.g. cross-correlation of RF data vs. cross-correlation of envelope data) could be used separately to determine the respective lengths of each of the coherent and incoherent averaging kernels.

As discussed above, motion compensation in accordance with embodiments of the present invention may comprise warping each of the RF frames in the series to one designated reference frame. Typically, this frame is designated as the most recently captured frame or most recently received frame. This is illustrated schematically in FIG. 10 which shows that all frames extending back to $R_{n-6}$ are warped to the latest captured frame $R_n$. This is typically preferred since, in the case of real-time data processing, warping to less recent frames causes an apparent delay or time lag in observable ultrasound images (if these are being generated from the warped RF frames in real-time). For instance, deliberate movement of the probe or changes in the scene being observed are reflected in the generated images only a few seconds later.

However motion tracking is typically less accurate when performed between frames which are greatly temporally separated. In the zero-latency case (i.e. the case where the most recent frame is the reference to which all others are warped), the maximum leap distance is equal to the entire size of the averaging kernel.

Figure 10:
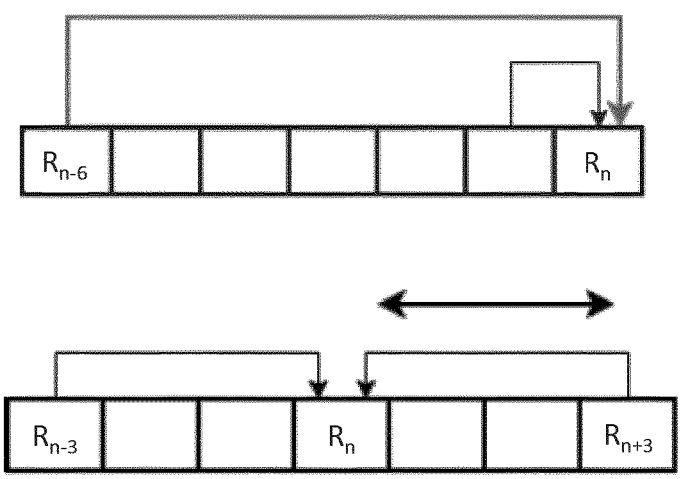
FIG. 10 schematically depicts a variation on one or more embodiments of the present invention.

In accordance with an alternative configuration therefore, the reference frame may instead be designated as a frame mid-way between the most recent frame in the series and the least recent frame in the series. This is illustrated in FIG. 10. Here, the reference frame $R_n$ is selected as a frame mid-way between the least recent frame $R_{n-3}$ and the most recent frame $R_{n+3}$.

In exchange for a few frames of latency (a few frames of time delay in rendered images), warping towards the center instead of the end reduces the temporal separation between frame $R_{n-6}$ and $R_n$ by half. The quality of the motion compensation is thereby increased. It should be noted that the computational cost of this configuration is no greater than that of a configuration in which the most recent frame is chosen as the reference frame.

For this implementation, assuming 2 cm/s lateral motion at 85 frames per second, very good performance is achieved both in terms of SNR increase and reduction of motion artefacts for 9 frames of persistence. However, as a trade-off, these settings do generate approximately 50 ms of latency in any generated ultrasound images.

As a further improvement upon the above method, a final step may be added to the process wherein the resulting coherent sum of the RF frames warped to the center or middle frame is then itself finally warped to the most recent frame. In this example, the steps are as follows. Each RF frame, as in the case above, is warped to the center frame in the series. The warped frames are then summed to generate a coherent sum of the warped RF frames. This coherent sum is then itself warped to the most recent frame (i.e. $R_{n+3}$) in the example of FIG. 10. This will fully eliminate the latency while keeping the benefits of the symmetrical kernel in terms of robustness to motion artifacts.

In all embodiments of the invention described, the RF frames (or data representations) may be representative of RF signal data which has been down-sampled or decimated. This process can introduce additional phase de-coherence, and phase information is lost when the down-sampling is performed. Image warping is generally based upon interpolation and resampling of data. Where phase information has been lost, it can be very difficult to recover full coherency between any warped RF frame and the reference RF frame.

In accordance with one or more embodiments of the invention, fully sampled data may be used for each RF frame, rather than for instance down-sampled data. Experimental evidence has shown that when using fully sampled data, fewer artifacts are generated when warping frames which have relatively large time lags between them. This means that, in embodiments described above in which RF frames are each warped to the most recent frame in the series (to minimize time lag), this procedure may be performed while producing fewer defects in resulting images.

In accordance with an aspect of the invention, there is provided a diagnostic imaging system comprising a processing unit adapted to carry out a signal processing method in accordance with any embodiment of the invention.

Figure 11:
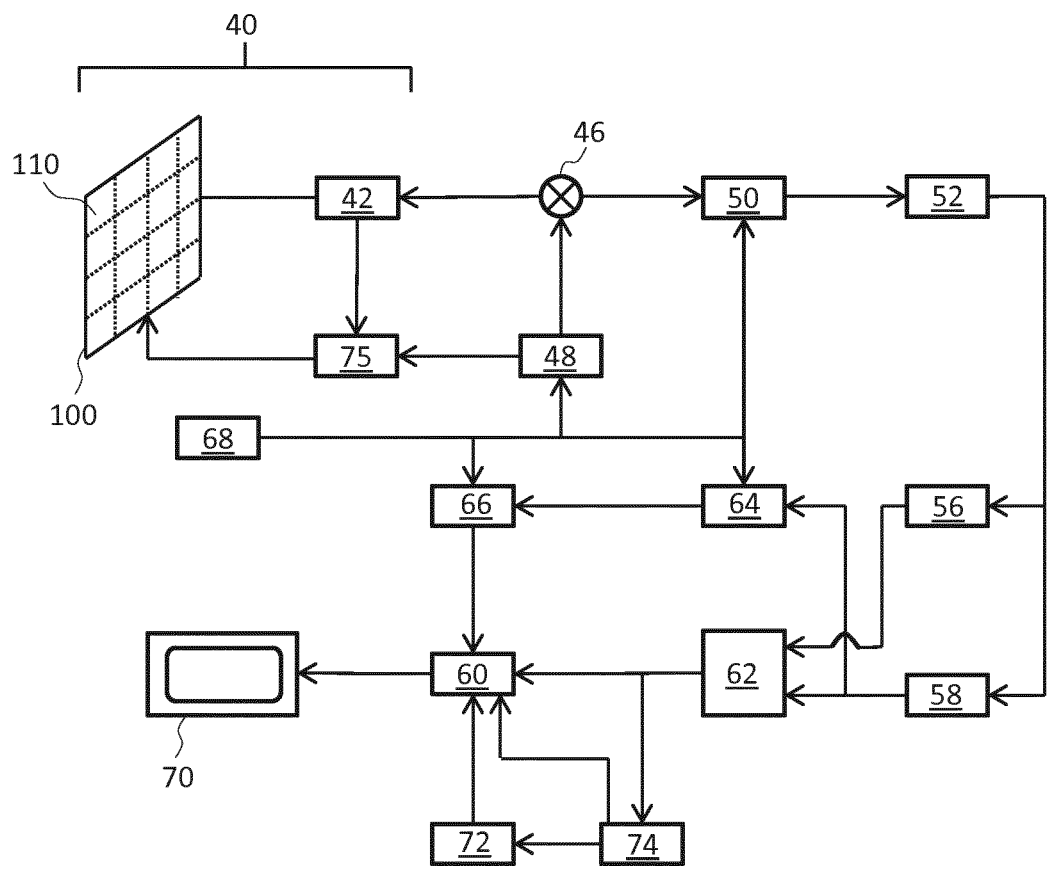
FIG. 11 schematically depicts an example ultrasound diagnostic imaging system.

The general operation of an exemplary ultrasound diagnostic imaging system will now be described, with reference to FIG. 11, and with emphasis on the signal processing function of the system since this invention relates to the processing of the signals measured by the transducer array.

The system comprises an array transducer probe 40 which has a CMUT transducer array 100 for transmitting ultrasound waves and receiving echo information. The transducer array 100 may alternatively comprise piezoelectric transducers formed of materials such as PZT or PVDF. The transducer array 100 is a two-dimensional array of transducers 110 capable of scanning in a 2D plane or in three dimensions for 3D imaging. In another example, the transducer array may be a 1D array.

The transducer array 100 is coupled to a microbeamformer 42 in the probe which controls reception of signals by the CMUT array cells or piezoelectric elements. Microbeamformers are capable of at least partial beamforming of the signals received by sub-arrays (or "groups" or "patches") of transducers as described in U.S. Pat. No. 5,997,479 (Savord et al.), U.S. Pat. No. 6,013,032 (Savord), and U.S. Pat. No. 6,623,432 (Powers et al.).

Note that the microbeamformer is entirely optional. The examples below assume no analog beamforming.

The microbeamformer 42 is coupled by the probe cable to a transmit/receive (T/R) switch 46 which switches between transmission and reception and protects the main beamformer 50 from high energy transmit signals when a microbeamformer is not used and the transducer array is operated directly by the main system beamformer. The transmission of ultrasound beams from the transducer array 40 is directed by a transducer controller 48 coupled to the microbeamformer by the T/R switch 46 and a main transmission beamformer (not shown), which receives input from the user's operation of the user interface or control panel 68.

One of the functions controlled by the transducer controller 48 is the direction in which beams are steered and focused. Beams may be steered straight ahead from (or-thogonal to) the transducer array, or at different angles for a wider field of view. The transducer controller 48 can be coupled to control a DC bias control 75 for the CMUT array. The DC bias control 75 sets DC bias voltage(s) that are applied to the CMUT cells.

In the reception channel, partially beamformed signals are produced by the microbeamformer 42 and are coupled to a main receive beamformer 50 where the partially beamformed signals from individual patches of transducers are combined into a fully beamformed signal. For example, the main beamformer 50 may have 128 channels, each of which receives a partially beamformed signal from a patch of dozens or hundreds of CMUT transducer cells or piezoelectric elements. In this way the signals received by thousands of transducers of a transducer array can contribute efficiently to a single beamformed signal.

The beamformed reception signals are coupled to a signal processing unit 52. This may be a signal processing unit in accordance with an aspect of the present invention. The signal processing unit 52 can process the received echo signals in various ways, such as band-pass filtering, decimation, I and Q component separation, and harmonic signal separation which acts to separate linear and nonlinear signals so as to enable the identification of nonlinear (higher harmonics of the fundamental frequency) echo signals returned from tissue and micro-bubbles. The signal processing unit may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting the noise at higher frequencies from greater depths where these frequencies are devoid of anatomical information.

The signal processing unit 52 is also adapted to perform one or more embodiments of the processing method of the present invention.

The beamformers for transmission and for reception are implemented in different hardware and can have different functions. Of course, the receiver beamformer is designed to take into account the characteristics of the transmission beamformer. In FIG. 11 only the receiver beamformers 42, 50 are shown, for simplicity. In the complete system, there will also be a transmission chain with a transmission micro beamformer, and a main transmission beamformer.

The function of the micro beamformer 42 is to provide an initial combination of signals in order to decrease the number of analog signal paths. This is typically performed in the analog domain.

The final beamforming is done in the main beamformer 50 and is typically after digitization.

The transmission and reception channels use the same transducer array 40' which has a fixed frequency band. However, the bandwidth that the transmission pulses occupy can vary depending on the transmission beamforming that has been used. The reception channel can capture the whole transducer bandwidth (which is the classic approach) or by using bandpass processing it can extract only the bandwidth that contains the useful information (e.g. the harmonics of the main harmonic).

The processed signals are coupled to a B mode (i.e. brightness mode, or 2D imaging mode) processing unit 56 and a Doppler processor 58. The B mode processor 56 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 58 processes temporally distinct signals from tissue movement and blood flow for the detection of the motion of substances such as the flow of blood cells in the image field. The Doppler processor 58 typically includes a wall filter with parameters which may be set to pass and/or reject echoes returned from selected types of materials in the body.

The structural and motion signals produced by the B mode and Doppler processors are coupled to a scan converter 62 and a multi-planar reformatter 74. The scan converter 62 arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field with their Doppler-estimated velocities to produce a color Doppler image which depicts the motion of tissue and blood flow in the image field. The multi-planar reformatter will convert echoes which are received from points in a common plane in a volumetric region of the body into an ultrasound image of that plane, as described in U.S. Pat. No. 6,443,896 (Detmer). A volume renderer 72 converts the echo signals of a 3D data set into a projected 3D image as viewed from a given reference point as described in U.S. Pat. No. 6,530,885 (Entrekin et al.).

The 2D or 3D images are coupled from the scan converter 62, multi-planar reformatter 74, and volume renderer 72 to an image processor 60 for further enhancement, buffering and temporary storage for display on an image display 70. In addition to being used for imaging, the blood flow values produced by the Doppler processor 58 and tissue structure information produced by the B mode processor 56 are coupled to a quantification processor 64. The quantification processor produces measures of different flow conditions such as the volume rate of blood flow as well as structural measurements such as the sizes of organs and gestational age. The quantification processor may receive input from the user control panel 68, such as the point in the anatomy of an image where a measurement is to be made. Output data from the quantification processor is coupled to a graphics processor 66 for the reproduction of measurement graphics and values with the image on the display 70, and for audio output from the display device 70. The graphics processor 66 can also generate graphic overlays for display with the ultrasound images. These graphic overlays can contain standard identifying information such as patient name, date and time of the image, imaging parameters, and the like. For these purposes the graphics processor receives input from the user interface 68, such as patient name. The user interface is also coupled to the transmit controller 48 to control the generation of ultrasound signals from the transducer array 40' and hence the images produced by the transducer array and the ultrasound system. The transmit control function of the controller 48 is only one of the functions performed. The controller 48 also takes account of the mode of operation (given by the user) and the corresponding required transmitter configuration and band-pass configuration in the receiver analog to digital converter. The controller 48 can be a state machine with fixed states.

The user interface is also coupled to the multi-planar reformatter 74 for selection and control of the planes of multiple multi-planar reformatted (MPR) images which may be used to perform quantified measures in the image field of the MPR images. As discussed above, embodiments make use of a controller and processing unit. These can each be implemented in numerous ways, with software and/or hardware, to perform the various functions required. A processor is one example of a controller or processing unit which employs one or more microprocessors that may be programmed using software (e.g., microcode) to perform the required functions. A controller or processing unit may however be implemented with or without employing a processor, and also may be implemented as a combination of dedicated hardware to perform some functions and a processor (e.g., one or more programmed microprocessors and associated circuitry) to perform other functions.

Examples of controller or processing unit components that may be employed in various embodiments of the present disclosure include, but are not limited to, conventional microprocessors, application specific integrated circuits (ASICs), and field-programmable gate arrays (FPGAs).

In various implementations, a processor or controller or processing unit may be associated with one or more storage media such as volatile and non-volatile computer memory such as RAM, PROM, EPROM, and EEPROM. The storage media may be encoded with one or more programs that, when executed on one or more processors and/or controllers and/or processing units, perform the required functions. Various storage media may be fixed within a processor or controller or processing unit or may be transportable, such that the one or more programs stored thereon can be loaded into a processor or controller or processing unit.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method of processing ultrasound signal data for use in generating ultrasound images, comprising:
controlling, by a processor, an ultrasound transducer array to obtain raw echo signals, wherein the ultrasound transducer array is operatively coupled to the processor;
receiving, by the processor, a plurality of raw echo signal representations of the raw echo signals, each of the plurality of raw echo signal representations representative of a same trajectory, section or volume through a body at different successive times;
applying, by the processor, a motion compensation procedure to the plurality of raw echo signal representations, the motion compensation procedure comprising:
designating, by the processor, a raw echo signal representation mid-way between a most recently received raw echo signal representation and a least recently received raw echo signal representation as a reference raw echo signal representation;
registering, by the processor, amplitude peaks of remaining raw echo signal representations to amplitude peaks of the reference raw echo signal representation to thereby derive a plurality of registered raw echo signal representations; and
aligning phases of the plurality of registered raw echo signal representations to one another to thereby derive a plurality of motion-compensated signal representations;
applying an averaging technique to one or more subsets of the plurality of motion-compensated signal representations to thereby derive one or more averaged signal representations;
generating, by the processor, one or more ultrasound images based on the one or more averaged signal representations; and
outputting, by the processor, the one or more ultrasound images on a display operatively coupled to the processor.

2. The method as claimed in claim 1, wherein the motion compensation procedure comprises a two-step process, comprising first registering amplitude peaks of the plurality of raw echo signal representations to one another, and subsequently applying a phase correction procedure to align phases of the plurality of raw echo signal representations to one another.

3. The method as claimed in claim 1,
wherein the one or more averaged signal representations comprise a plurality of averaged signal representations, and
wherein the method further comprises:
processing said plurality of averaged signal representations to generate a corresponding plurality of averaged envelope signal representations or ultrasound images; and
applying a further averaging technique to said plurality of averaged envelope signal representations or ultrasound images.

4. The method as claimed in claim 1,
wherein the plurality of raw echo signal representations are received non-simultaneously.

5. The method as claimed in claim 4, wherein, subsequent to deriving the one or more averaged signal representations, a motion compensation procedure is applied to said one or more averaged signal representations comprising at least registering amplitude peaks of the one or more averaged signal representations to those of a most recently received raw echo signal representation.

6. The method as claimed in claim 2, wherein the motion compensation procedure comprises:
processing the plurality of raw echo signal representations to derive a corresponding plurality of envelope signal representations;
determining deviations between the plurality of envelope signal representations;
performing adjustments to the plurality of raw echo signal representations based on the determined deviations, so as to register the amplitude peaks of the plurality of raw echo signal representations with one another and to thereby derive the plurality of registered raw echo signal representations; and
applying the phase correction procedure to the plurality of registered raw echo signal representations so as to register the phases of the plurality of registered raw echo signal representations to one another.

7. The method as claimed in claim 6, wherein said determining deviations between the plurality of envelope signal representations comprises:
determining deviations between temporally consecutive pairs at least a subset of the plurality of envelope signal representations, said the subset including one envelope signal representation designated as a reference envelop signal representation;
adding, to each of the deviations between temporally consecutive pairs, a sum of all preceding or succeeding determined deviations up to the reference envelope signal representation, such as to derive, for each envelope signal representation, cumulative deviations with respect to the reference envelope signal representation, and
adjusting the plurality of raw echo signal representations, based on the determined cumulative deviations for the plurality of envelope signal representations, to thereby achieve registration of the amplitude peaks of the plurality of raw echo signal representations.

8. The method as claimed in claim 1, wherein the motion compensation procedure comprises:
determining deviations between signal the amplitude peaks of the plurality of raw echo signal representations;
performing adjustments to the plurality of raw echo signal data representations based on said determined deviations, so as to:
achieve registration of the amplitude peaks of the different plurality of raw echo signal representations to one another and derive the plurality of registered raw echo signal representations, and
alignment of the phases of the plurality of registered raw echo signal representations to one another.

9. The method as claimed in claim 2, wherein said phase correction procedure comprises:
determining a phase shift between at least a subset of the plurality of raw echo signal representations and the reference raw echo signal representation; and
adjusting the phases of each of the plurality of raw echo signal representations in accordance with the determined phase shifts.

10. The method as claimed in claim 1, further comprising:
determining, following said motion compensation procedure, a measure of similarity between the plurality of raw echo signal representations; and
determining, based on said measure of similarity, a total number of raw echo signal representations to be included in each of said one or more subsets to which the averaging technique is applied.

11. The method as claimed in claim 1,
wherein said averaging technique comprises determining a weighted average of the plurality of motion compensated signal representations, and
wherein the method further comprises:
determining, following application of said motion compensation procedure, a measure of similarity between each raw echo signal representation and the reference raw echo signal representation; and
determining a weighting factor for each raw echo signal representation based on the determined measure of similarity for said raw echo signal representation, the weighting factors for use in determining said weighted average of the plurality of motion compensated signal representations.

12. The method as claimed in claim 1, wherein each raw echo signal representation comprises data corresponding to a plurality of individual echo signals.

13. The method as claimed in claim 1, further comprising wherein generating the ultrasound image comprises processing the one or more averaged data signal representations to form the one or more ultrasound images.

14. An ultrasound diagnostic imaging system, comprising:
an ultrasound transducer array; and
a processor operatively coupled with the ultrasound transducer array, wherein the processor is adapted to:
control the ultrasound transducer array to obtain raw echo signals;
receive a plurality of raw echo signal representations of the raw echo signals, each of the plurality of raw echo signal representations representative of a same trajectory, section or volume through a body at different successive times;
apply a motion compensation procedure to the plurality of raw echo signal representations, the motion compensation procedure comprising:
designating a raw echo signal representation midway between a most recently received raw echo signal representation and a least recently received raw echo signal representation as a reference raw echo signal representation;
registering amplitude peaks of remaining raw echo signal representations to amplitude peaks of the reference raw echo signal representation to thereby derive a plurality of registered raw echo signal representations; and
aligning phases of the plurality of registered raw echo signal representations to one another to thereby derive a plurality of motion-compensated signal representations;
apply an averaging technique to one or more subsets of the plurality of motion-compensated signal representations to thereby derive one or more averaged signal representations;
generate one or more ultrasound images based on the one or more averaged signal representations; and
output the one or more ultrasound images on a display operatively coupled to the processor.

15. The method as claimed in claim 9, wherein a phase shift for each given raw echo signal representation $f_i$ is determined based on the expression $\alpha = \angle(K \otimes (f_0 \cdot f_i^*))$, where $\alpha$ is a set of phase shifts, K is a convolution kernel, and $f_0$ is the reference raw echo signal representation.

16. The method as claimed in claim 10, wherein the total number of the raw echo signal representations included in each of said one or more subsets to which the averaging technique is applied is positively related to said determined measure of similarity.

17. The method as claimed in claim 11,
wherein said weighting factors are binary weighting factors,
wherein each motion compensated signal representation is only included as part of the weighted average in the case that its measure of similarity with respect to the reference raw echo signal representation is above a certain threshold.

18. The method as claimed in claim 12, wherein said plurality of individual echo signals are representative of a set of adjacent paths through said body, so as to form a representation of a section or a volume through the body.

* * * * *